(12) United States Patent
Bartning et al.

(10) Patent No.: US 7,892,163 B2
(45) Date of Patent: Feb. 22, 2011

(54) METHOD OF TREATING URINARY INCONTINENCE

(75) Inventors: Michelle Bartning, Santa Rosa, CA (US); Kevin F. Gironda, Schwenksville, PA (US); Mari Hou, Basking Ridge, NJ (US); Thomas P. Luchino, Freehold, NJ (US); Kirsten Freislinger Luehrs, Palo Alto, CA (US); Pramod Mavinkurve, Princeton, NJ (US); Leonard Rosenfeld, Yardley, PA (US); Raymond J. Hull, Jr., Hampton, NJ (US); David J. Chase, Somerville, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 74 days.

(21) Appl. No.: 11/776,185

(22) Filed: Jul. 11, 2007

(65) Prior Publication Data
US 2008/0033231 A1 Feb. 7, 2008

Related U.S. Application Data

(63) Continuation-in-part of application No. 11/456,424, filed on Jul. 10, 2006, and a continuation-in-part of application No. 11/456,433, filed on Jul. 10, 2006, now Pat. No. 7,717,892, and a continuation-in-part of application No. 11/456,442, filed on Jul. 10, 2006.

(51) Int. Cl.
*A61F 2/00* (2006.01)

(52) U.S. Cl. ........................................ 600/29

(58) Field of Classification Search ................ 128/885; 600/29–32; 604/330–331
See application file for complete search history.

(56) References Cited

U.S. PATENT DOCUMENTS

| | | | |
|---|---|---|---|
| 4,139,006 A | 2/1979 | Corey |
| 4,290,420 A | 9/1981 | Manetta |
| 4,669,478 A | 6/1987 | Robertson |
| 4,677,967 A | 7/1987 | Zartman |
| 4,733,665 A | 3/1988 | Palmaz |
| 4,739,762 A | 4/1988 | Palmaz |
| 4,776,337 A | 10/1988 | Palmaz |
| 4,856,516 A | 8/1989 | Hillstead |
| 4,875,898 A | 10/1989 | Eakin |
| 4,920,986 A | 5/1990 | Biswas |
| 4,986,823 A | 1/1991 | Anderson |
| 5,007,894 A | 4/1991 | Enhorning |
| 5,036,867 A | 8/1991 | Biswas |
| 5,041,077 A | 8/1991 | Kulick |

(Continued)

FOREIGN PATENT DOCUMENTS

AU 684733 B 7/1994

(Continued)

*Primary Examiner*—Charles A Marmor, II
*Assistant Examiner*—Christine D Hopkins

(57) ABSTRACT

A method for treating urinary incontinence includes the steps of inserting into the woman's vagina a first disposable device, removing the first disposable device, and inserting a second disposable device substantially identical to the first disposable device. The disposable devices have a working portion with opposed working surfaces to provide support to an associated urinary system and an anchoring portion to maintain the disposable device in place during use. The anchoring portion has at least one member extending beyond at least one end of the working portion.

14 Claims, 8 Drawing Sheets

U.S. PATENT DOCUMENTS

| | | |
|---|---|---|
| 5,045,079 A | 9/1991 | West |
| 5,102,417 A | 4/1992 | Palmaz |
| 5,116,365 A | 5/1992 | Hillstead |
| 5,224,494 A | 7/1993 | Enhorning |
| 5,234,456 A | 8/1993 | Silvestrini |
| 5,306,294 A | 4/1994 | Winston |
| 5,366,504 A | 11/1994 | Andersen |
| 5,387,206 A | 2/1995 | Valentine |
| 5,425,765 A | 6/1995 | Tiefenbrun |
| 5,494,029 A | 2/1996 | Lane |
| 5,514,176 A | 5/1996 | Bosley, Jr. |
| 5,540,713 A | 7/1996 | Schnepp Pesch |
| 5,545,209 A | 8/1996 | Roberts |
| 5,591,199 A | 1/1997 | Porter |
| 5,593,442 A | 1/1997 | Klein |
| 5,601,593 A | 2/1997 | Freitag |
| 5,603,685 A | 2/1997 | Tutrone, Jr. |
| 5,603,698 A | 2/1997 | Roberts |
| 5,607,445 A | 3/1997 | Summers |
| 5,611,768 A | 3/1997 | Tutrone, Jr. |
| 5,618,256 A | 4/1997 | Reimer |
| 5,618,301 A | 4/1997 | Hauenstein |
| 5,628,787 A | 5/1997 | Mayer |
| 5,628,788 A | 5/1997 | Pinchuk |
| 5,643,312 A | 7/1997 | Fischell |
| 5,645,559 A | 7/1997 | Hachtman |
| 5,674,241 A | 10/1997 | Bley |
| 5,690,670 A | 11/1997 | Davidson |
| 5,695,517 A | 12/1997 | Marin |
| 5,697,971 A | 12/1997 | Fischell |
| 5,716,396 A | 2/1998 | Williams, Jr. |
| 5,723,003 A | 3/1998 | Winston |
| 5,749,918 A | 5/1998 | Hogendijk |
| 5,776,161 A | 7/1998 | Globerman |
| 5,779,729 A | 7/1998 | Severini |
| 5,785,640 A | 7/1998 | Kresch |
| 5,788,979 A | 8/1998 | Alt |
| 5,800,338 A | 9/1998 | Kollerup |
| 5,800,519 A | 9/1998 | Sandock |
| 5,800,520 A | 9/1998 | Fogarty |
| 5,813,973 A | 9/1998 | Gloth |
| 5,814,063 A | 9/1998 | Freitag |
| 5,817,100 A | 10/1998 | Igaki |
| 5,820,918 A | 10/1998 | Ronan |
| 5,827,321 A | 10/1998 | Roubin |
| 5,833,707 A | 11/1998 | McIntyre |
| 5,840,081 A | 11/1998 | Andersen |
| 5,843,161 A | 12/1998 | Solovay |
| 5,843,176 A | 12/1998 | Weier |
| 5,855,600 A | 1/1999 | Alt |
| 5,873,906 A | 2/1999 | Lau |
| 5,879,370 A | 3/1999 | Fischell |
| 5,879,381 A | 3/1999 | Moriuchi |
| 5,888,201 A | 3/1999 | Stinson |
| 5,891,191 A | 4/1999 | Stinson |
| 5,895,406 A | 4/1999 | Gray |
| 5,902,332 A | 5/1999 | Schatz |
| 5,911,732 A | 6/1999 | Hojeibane |
| 5,911,752 A | 6/1999 | Dustrude |
| 5,913,897 A | 6/1999 | Corso, Jr. |
| 5,922,019 A | 7/1999 | Hankh |
| 5,922,020 A | 7/1999 | Klein |
| 5,925,353 A | 7/1999 | Mosseri |
| 5,938,682 A | 8/1999 | Hojeibane |
| 5,948,191 A | 9/1999 | Solovay |
| 5,957,949 A | 9/1999 | Leonhardt |
| 5,976,152 A | 11/1999 | Regan |
| 5,980,553 A | 11/1999 | Gray |
| 5,988,169 A | 11/1999 | Anderson |
| 5,997,467 A | 12/1999 | Connolly |
| 6,013,036 A | 1/2000 | Caillouette |
| 6,019,779 A | 2/2000 | Thorud |
| 6,030,375 A | 2/2000 | Anderson |
| 6,035,238 A | 3/2000 | Ingle et al. |
| 6,048,306 A | 4/2000 | Spielberg |
| 6,053,940 A | 4/2000 | Wijay |
| 6,063,113 A | 5/2000 | Kavteladze et al. |
| 6,086,604 A | 7/2000 | Fischell |
| 6,090,038 A | 7/2000 | Zunker |
| 6,090,098 A | 7/2000 | Zunker |
| 6,106,530 A | 8/2000 | Harada |
| 6,110,099 A | 8/2000 | Benderev |
| 6,129,755 A | 10/2000 | Mathis |
| 6,142,928 A | 11/2000 | Zunker |
| 6,158,435 A | 12/2000 | Dorsey |
| 6,162,243 A | 12/2000 | Gray |
| 6,176,872 B1 | 1/2001 | Miksza |
| 6,183,456 B1 | 2/2001 | Brown |
| 6,189,535 B1 | 2/2001 | Enhorning |
| 6,190,403 B1 | 2/2001 | Fischell |
| 6,190,406 B1 | 2/2001 | Duerig |
| 6,197,051 B1 | 3/2001 | Zhong |
| 6,210,429 B1 | 4/2001 | Vardi |
| 6,241,738 B1 | 6/2001 | Dereume |
| 6,245,103 B1 | 6/2001 | Stinson |
| 6,251,134 B1 | 6/2001 | Alt |
| 6,254,627 B1 | 7/2001 | Freidberg |
| 6,254,633 B1 | 7/2001 | Pinchuk |
| 6,261,305 B1 | 7/2001 | Marotta |
| 6,270,524 B1 | 8/2001 | Kim |
| 6,273,895 B1 | 8/2001 | Pinchuk |
| 6,287,315 B1 | 9/2001 | Wijeratne |
| 6,319,275 B1 | 11/2001 | Lashinski |
| 6,325,825 B1 | 12/2001 | Kula |
| 6,350,248 B1 | 2/2002 | Knudson |
| 6,375,676 B1 | 4/2002 | Cox |
| 6,415,484 B1 | 7/2002 | Moser |
| 6,418,930 B1 | 7/2002 | Fowler |
| 6,423,091 B1 | 7/2002 | Hojeibane |
| 6,436,428 B1 | 8/2002 | Mahashabde |
| 6,458,072 B1 | 10/2002 | Zunker |
| 6,460,542 B1 | 10/2002 | James |
| 6,462,169 B1 | 10/2002 | Shalaby |
| 6,470,890 B1 | 10/2002 | Diokno |
| 6,478,726 B1 | 11/2002 | Zunker |
| 6,478,813 B1 | 11/2002 | Keith |
| 6,488,702 B1 | 12/2002 | Besselink |
| 6,503,190 B1 | 1/2003 | Ulmsten |
| 6,530,951 B1 | 3/2003 | Bates |
| 6,537,293 B1 | 3/2003 | Berryman |
| 6,540,775 B1 | 4/2003 | Fischell |
| 6,547,817 B1 | 4/2003 | Fischell |
| 6,558,370 B2 | 5/2003 | Moser |
| 6,562,064 B1 | 5/2003 | deBeer |
| 6,562,067 B2 | 5/2003 | Mathis |
| 6,572,643 B1 | 6/2003 | Gharibadeh |
| 6,585,773 B1 | 7/2003 | Xie |
| 6,605,111 B2 | 8/2003 | Bose |
| 6,605,294 B2 | 8/2003 | Sawhney |
| 6,612,977 B2 | 9/2003 | Staskin |
| 6,645,136 B1 | 11/2003 | Zunker |
| 6,645,137 B2 | 11/2003 | Ulmsten |
| 6,652,544 B2 | 11/2003 | Houser |
| 6,666,881 B1 | 12/2003 | Richter |
| 6,669,707 B1 | 12/2003 | Swanstrom |
| 6,676,594 B1 | 1/2004 | Zunker |
| 6,676,692 B2 | 1/2004 | Rabkin |
| 6,676,694 B1 | 1/2004 | Weiss |
| 6,679,831 B1 | 1/2004 | Zunker |
| 6,695,763 B2 | 2/2004 | Zunker |
| 6,695,876 B1 | 2/2004 | Marotta |
| 6,699,274 B2 | 3/2004 | Stinson |
| 6,702,846 B2 | 3/2004 | Mikus et al. |
| 6,739,340 B1 | 5/2004 | Jensen |

| | | |
|---|---|---|
| 6,764,503 B1 | 7/2004 | Ishimaru |
| 6,770,025 B2 | 8/2004 | Zunker |
| 6,786,904 B2 | 9/2004 | Döscher |
| 6,808,485 B2 | 10/2004 | Zunker |
| 6,881,222 B2 | 4/2005 | White |
| 6,997,952 B2 | 2/2006 | Furukawa et al. |
| 7,036,511 B2 | 5/2006 | Nissenkorn |
| 7,214,219 B2 | 5/2007 | Intravartolo et al. |
| 2001/0007081 A1 | 7/2001 | Caprio |
| 2001/0016726 A1 | 8/2001 | Dubrul |
| 2001/0053932 A1 | 12/2001 | Phelps |
| 2002/0032486 A1 | 3/2002 | Lazarovitz |
| 2002/0068975 A1 | 6/2002 | Teitelbaum |
| 2002/0082610 A1 | 6/2002 | Cioanta |
| 2002/0083949 A1 | 7/2002 | James |
| 2002/0087176 A1 | 7/2002 | Greenhalgh |
| 2002/0087186 A1 | 7/2002 | Shelso |
| 2002/0116046 A1 | 8/2002 | DiCaprio |
| 2002/0133183 A1 | 9/2002 | Lentz |
| 2002/0138134 A1 | 9/2002 | Kim |
| 2002/0156343 A1 | 10/2002 | Zunker |
| 2002/0165521 A1 | 11/2002 | Cioanta |
| 2002/0179093 A1 | 12/2002 | Adamkiewicz |
| 2002/0183711 A1 | 12/2002 | Moser |
| 2003/0015203 A1 | 1/2003 | Makower |
| 2003/0018377 A1 | 1/2003 | Berg |
| 2003/0040754 A1 | 2/2003 | Mitchell |
| 2003/0040771 A1 | 2/2003 | Hyodoh |
| 2003/0125603 A1 | 7/2003 | Zunker |
| 2003/0187494 A1 | 10/2003 | Loaldi |
| 2004/0049211 A1 | 3/2004 | Tremulis |
| 2004/0077924 A1 | 4/2004 | Zunker |
| 2004/0078013 A1 | 4/2004 | Zunker |
| 2004/0122285 A1 | 6/2004 | Zunker |
| 2004/0148010 A1 | 7/2004 | Rush |
| 2004/0158122 A1 | 8/2004 | Guerquin |
| 2004/0210211 A1 | 10/2004 | Devens |
| 2004/0230284 A1 | 11/2004 | Headley |
| 2004/0249238 A1 | 12/2004 | Farrell |
| 2004/0249433 A1 | 12/2004 | Freitag |
| 2004/0267280 A1 | 12/2004 | Nishide |
| 2005/0010285 A1 | 1/2005 | Lambrecht |
| 2005/0016545 A1 | 1/2005 | Nissenkorn |
| 2005/0085923 A1 | 4/2005 | Levine |
| 2005/0096673 A1 | 5/2005 | Stack |
| 2005/0096721 A1 | 5/2005 | Mangin |
| 2005/0096732 A1 | 5/2005 | Marotta |
| 2005/0125020 A1 | 6/2005 | Meade et al. |
| 2005/0250978 A1 * | 11/2005 | Kammerer .................. 600/29 |
| 2006/0100478 A1 | 5/2006 | Connors et al. |
| 2007/0203429 A1 | 8/2007 | Ziv |
| 2008/0009662 A1 | 1/2008 | Bartning et al. |
| 2008/0009663 A1 | 1/2008 | Bartning et al. |
| 2008/0009664 A1 | 1/2008 | Bartning et al. |
| 2008/0009666 A1 | 1/2008 | Bartning et al. |
| 2008/0009814 A1 | 1/2008 | Bartning et al. |
| 2008/0009931 A1 | 1/2008 | Bartning et al. |
| 2008/0033230 A1 | 2/2008 | Bartning et al. |
| 2008/0281149 A1 | 11/2008 | Sinai et al. |
| 2009/0203959 A1 | 8/2009 | Ziv et al. |
| 2009/0266367 A1 | 10/2009 | Ziv et al. |

FOREIGN PATENT DOCUMENTS

| | | |
|---|---|---|
| EP | 0 264 258 A | 4/1988 |
| EP | 0 498 912 A | 8/1992 |
| EP | 0 363 421 B | 9/1992 |
| EP | 0 556 908 A | 8/1993 |
| EP | 0 625 890 A | 11/1994 |
| EP | 0 663 197 A | 7/1995 |
| EP | 0 663 197 B | 7/1995 |
| EP | 0 700 669 A | 3/1996 |
| EP | 0 737 048 A | 10/1996 |
| EP | 0 955 024 A | 11/1999 |
| EP | 0 963 217 B | 12/2004 |
| GB | 2364645 A | 2/2002 |
| WO | WO 95/05790 A | 3/1995 |
| WO | WO 97/34550 A | 9/1997 |
| WO | WO 98/34677 A | 8/1998 |
| WO | WO 98/42281 A | 10/1998 |
| WO | WO 99/22680 A | 5/1999 |
| WO | WO 99/59477 A | 11/1999 |
| WO | WO 00/03659 A | 1/2000 |
| WO | WO 00/67662 A | 11/2000 |
| WO | WO 01/67983 A | 9/2001 |
| WO | WO 01/70154 A | 9/2001 |
| WO | WO 02/26160 A | 4/2002 |
| WO | WO 02/28313 A | 4/2002 |
| WO | WO 03/047476 A | 6/2003 |
| WO | WO 2004/103213 A | 12/2004 |
| WO | WO 2005/087153 A | 9/2005 |
| WO | WO 2005/087154 A | 9/2005 |
| WO | WO 2006/097935 A | 9/2006 |
| WO | 2008/010214 A | 1/2008 |
| WO | 2008/152628 A | 12/2008 |
| WO | WO 2009/044394 A | 4/2009 |
| WO | 2009/130702 A | 10/2009 |

* cited by examiner

METHOD OF TREATING URINARY INCONTINENCE

CROSS-REFERENCE TO RELATED APPLICATIONS

This application is a continuation-in-part of U.S. application Ser. No. 11/456,424 filed Jul. 10, 2006, and is a continuation-in-part of U.S. application Ser. No. 11/456,433 filed Jul. 10, 2006 now U.S. Pat. No. 7,717,892, and is a continuation-in-part of U.S. application Ser. No. 11/456,442 filed Jul. 10, 2006, the complete disclosures of which are hereby incorporated herein by reference for all purposes.

BACKGROUND OF THE INVENTION

1. Field of the Invention

The present invention relates to a method for treating urinary incontinence. More specifically, this invention relates to a method for utilizing a device that has a working portion an anchoring portion for retention in the vagina. The device reduces or prevents urinary incontinence.

2. Description of the Prior Art

Stress urinary incontinence is a problem for many women. It is characterized by leakage of urine during a stressing event, such as a cough or a sneeze. Many devices have been designed to reduce or prevent stress urinary incontinence. U.S. Pat. No. 5,603,685 teaches inflatable devices and a means to provide a device that is small for insertion into the vagina and enlarges to a required shape and pressure to reduce or prevent urinary incontinence. U.S. Pat. No. 6,090,098 teaches tampon-like devices, each made with a combination of absorbing and/or non-absorbing fibrous materials. U.S. Pat. No. 6,645,137 teaches a coil that expands in the vagina. U.S. Pat. No. 5,036,867 teaches a compressible resilient pessary. U.S. Pat. No. 6,460,542 teaches a highly shaped rigid pessary. Many patents are drawn to stents that are sized and designed to keep arteries open.

Despite the teaching of the prior art, there is a continuing need for a method for reducing or preventing urinary incontinence.

SUMMARY OF THE INVENTION

We have addressed the needs discussed above with the present invention's method that includes the steps of inserting into the woman's vagina a first disposable device, removing the first disposable device, and inserting a second disposable device substantially identical to the first disposable device. The disposable devices have a working portion with opposed working surfaces to provide support to an associated urinary system and an anchoring portion to maintain the disposable device in place during use. The anchoring portion has at least one member extending beyond at least one end of the working portion.

DETAILED DESCRIPTION OF PREFERRED EMBODIMENTS

As used herein the specification and the claims, the term "wire form" and variants thereof relate to a structure formed of at least one wire or wire-like material that is manipulated and optionally secured (e.g., by welding) in a desired three-dimensional structure.

As used herein the specification and the claims, the term "shape memory material" and variants thereof relate to materials that can be shaped into an initial shape, which initial shape can be subsequently formed into a stable second shape. The material is capable of substantially reverting to its initial shape upon exposure to an appropriate event, including without limitation mechanical deformation and a change in temperature.

As used herein the specification and the claims, the term "stent" and variants thereof relate to a device used to support a bodily orifice, cavity, vessel, and the like. The stent is resilient, flexible, and collapsible with memory. The stent may be any suitable form, including, but not limited to, scaffolding, a slotted tube or a wire form.

As used herein, a "stent" is a device used to support a bodily orifice, cavity, vessel, and the like. The stent is resilient, flexible, and collapsible with memory. The stent may be any suitable form, including, but not limited to, scaffolding, a slotted tube or a wire form.

Figure 1:
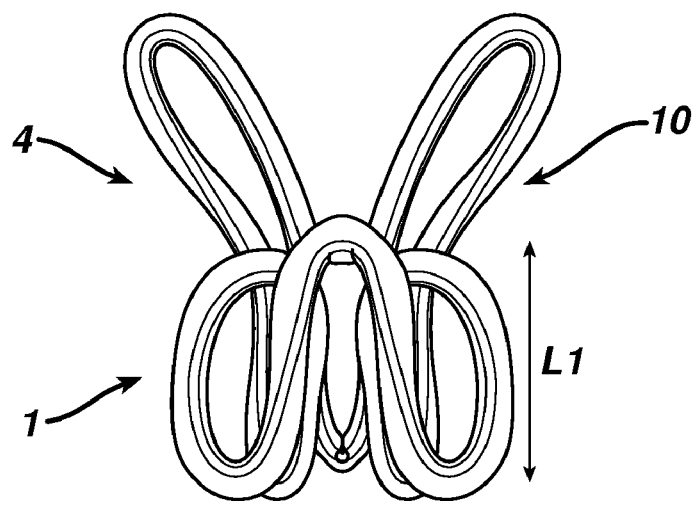
FIG. 1 is a perspective view of a device according to the present invention.
Figure 2:
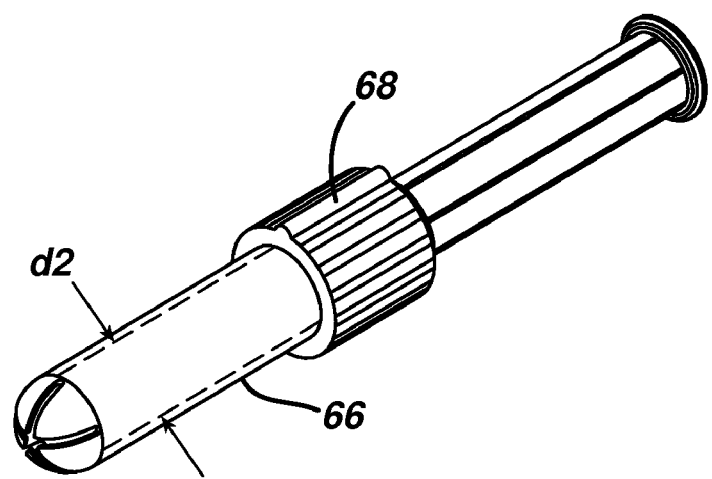
FIG. 2 is a perspective view of the device of FIG. 1 in the insertion state while contained in an applicator.
Figure 3:
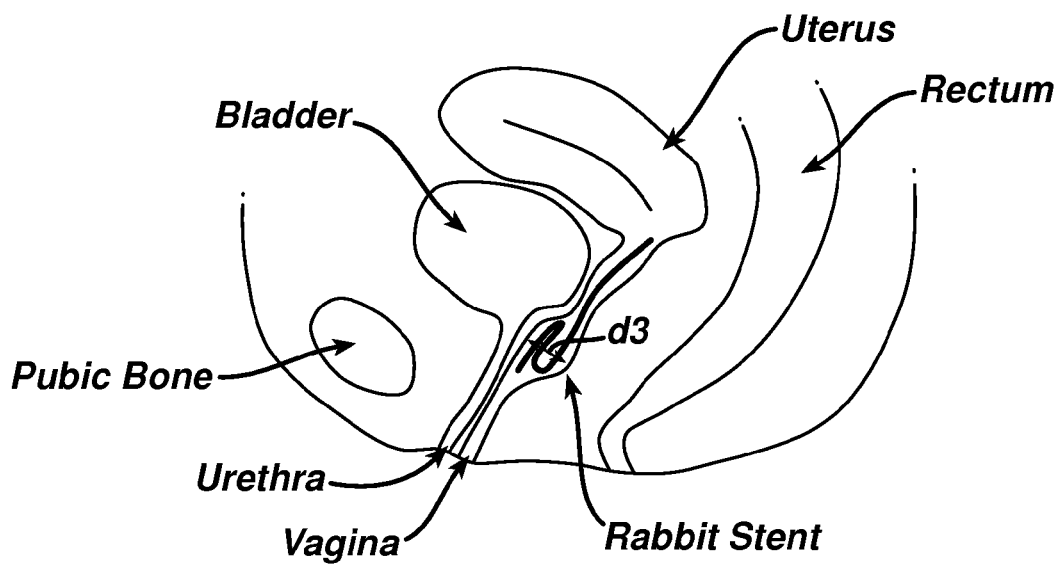
FIG. 3 is a perspective view of the device of FIG. 1 in the use state.
Figure 4:
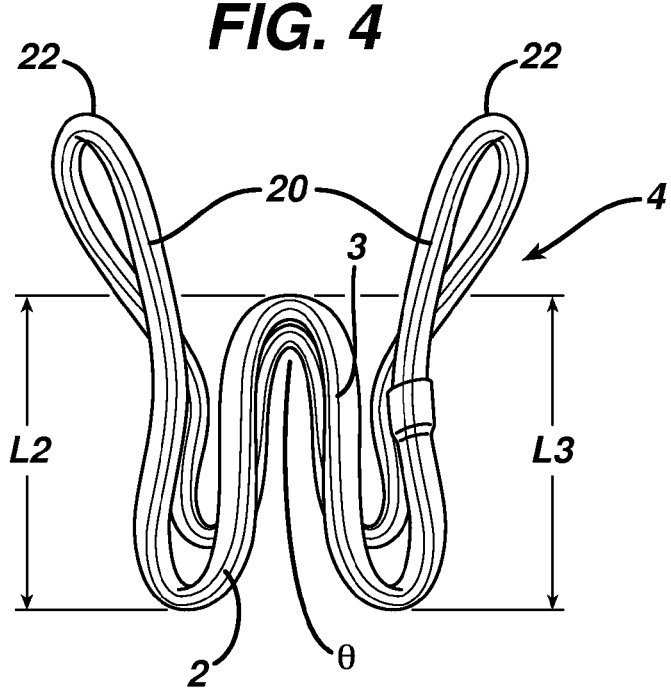
FIG. 4 is a perspective view of a second device according to the present invention.
Figure 5:
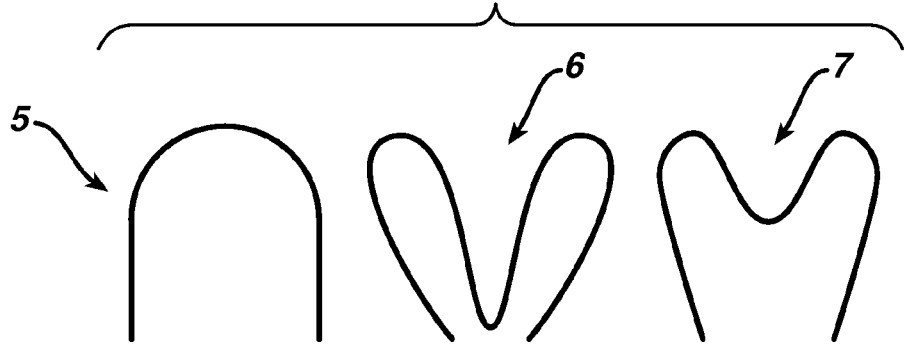
FIG. 5 illustrates several plan views of an anchoring portion according to the present invention.
Figure 6A:
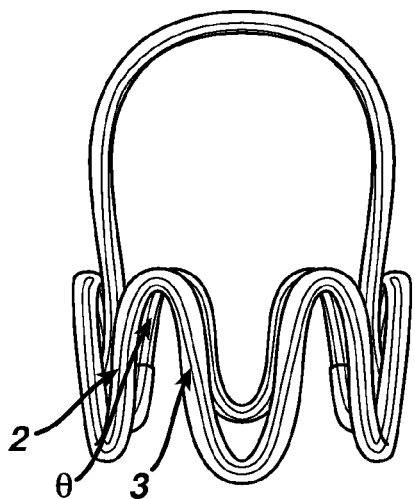
FIG. 6A is a perspective view of a third device according to the present invention.
Figure 6B:
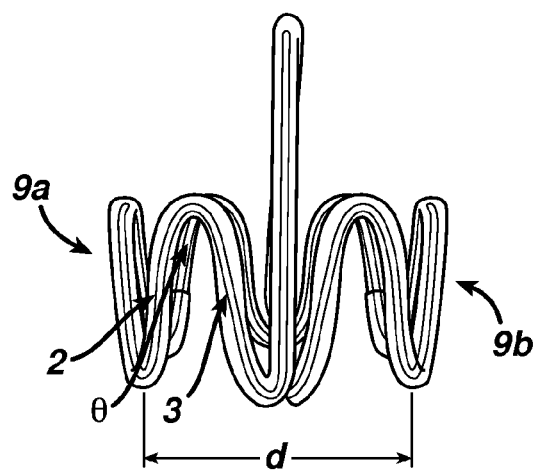
FIG. 6B is a side elevation of the device of FIG. 6A.
Figure 7:
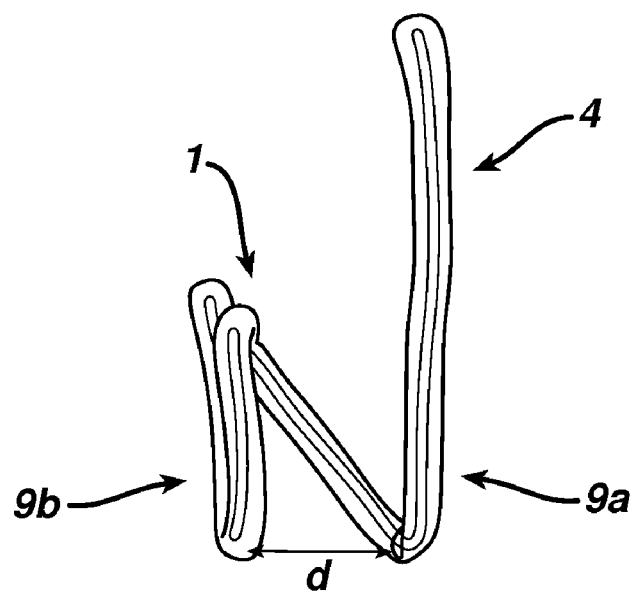
FIG. 7 is a side view of the device of FIG. 1.

Referring to FIGS. 1-8, there is shown a device 10 that is useful in the method of the present invention. The device 10 has a working portion 1 which is generally cylindrical in shape and contains working surfaces 9 a and 9 b. Working portion 1 has an initial equivalent diameter d ranging from 20 mm to 170 mm and a length L1 ranging from 10 mm to 60 mm. Where the working portion is non-cylindrical, the equivalent diameter is the maximum distance in millimeters between the opposed working surfaces. As seen in FIG. 2, working portion 1 has an insertion (in an applicator or other device for insertion) equivalent diameter d 2 ranging from 5 mm to 20 mm. As seen in FIG. 3, working portion 1 has a use equivalent diameter (in the vagina) d 3 ranging from 5 mm to 40 mm. Working portion 1 may be made of any elastic material that compresses and recovers with sufficient force to provide the desired effect. In one embodiment, the working portion 1 is made of Nitinol wire 20 and comprises alternating sinusoidal struts 2, 3 that intersect and form a strut angle θ. Alternating struts 2, 3 have a length L2 and L3 equal to the working portion length. The working pressure exerted by working portion 1 is determined by the thickness of the wire, the number of wires, the length of the struts and the strut angle, and the number of times the working portion is heat-treated. The number of wires may range from about 1 to about 20. The wires may be separate, twisted, or braided. For some applications, the working portion exerts a pressure of from 5 to 250 cm $H_2O$ in the working state. Device 10 may also have an anchoring portion 4. Anchoring portion 4 is designed to keep the device in place when in use. Anchoring portion 4 is shaped suitable to keep the device in place while in use. Suitable shapes include, but are not limited to, a basket handle 5, rabbit ears 6, and a dog bone 7, as shown in the FIG. 5. The anchoring portion may be made of the same material as the working portion or they may be made of different materials. The working portion and anchoring portion may be made as a uni-body construction, or may be made separately and joined by attachment means, such as silicone tubing 22. The devices may be treated to provide improved biocompatibility. The device may be placed inside tubing, for example silicone tubing, or may be dip coated in suitable polymeric materials.

Devices according to the present invention may be useful for treating or preventing urinary incontinence. For this application, the device is sized to fit comfortably in the vagina. All of the devices described below may have working portions with initial equivalent diameters of from about 20 to about 170 mm. Preferably, the working portion has a generally cylindrical working portion that may have an initial equivalent diameter ranging from about 20 to about 170 mm, preferably about 20 to about 45 mm, or more preferably about 30 mm; an insertion equivalent diameter ranging from about 5 to about 25 mm, preferably about 10 to about 20 mm, or more preferably about 18 mm; a use equivalent diameter ranging from about 20 to about 40 mm, preferably about 25 to about 30 mm, or more preferably about 25 mm; and a length ranging from about 20 to about 60 mm, preferably about 20 to about 30 mm, or more preferably about 25 mm. The anchoring portion extends beyond the working portion and may have an initial equivalent diameter ranging from about 20 to about 60 mm, preferably about 40 to about 60 mm, or more preferably about 50 mm; an insertion equivalent diameter ranging from about 10 to about 25 mm, preferably about 10 to about 20 mm, or more preferably about 18 mm; a use equivalent diameter ranging from about 20 to about 60 mm, preferably about 40 to about 60 mm, or more preferably about 50 mm; and a length ranging from about 10 to about 50 mm, preferably about 20 to about 40 mm, or more preferably about 30 mm.

For a basket stent, the working member of the device has a length and equivalent diameter in the insertion state, the working state, and the removal state. The insertion state length may range from about 20 to about 30 mm, for example about 25 mm. The insertion state equivalent diameter may range from about 5 to about 20 mm, for example about 18 mm. The working state length at rest and during a cough may range from about 20 to about 30 mm, for example about 25 mm. The working state equivalent diameter at rest may range from about 20 to about 30 mm, for example about 25 mm. The working state equivalent diameter during a cough may range from about 15 to about 25 mm, for example about 20 mm. The removal state length may range from about 20 to about 30 mm, for example about 25 mm. The removal state equivalent diameter may range from about 15 to about 20 mm, for example about 18 mm.

The anchoring portion of the device has a length and width in the insertion state, the working state, and the removal state. The insertion state length may range from about 25 to about 40 mm, for example about 30 mm. The insertion state width may range from about 15 to about 20 mm, for example about 18 mm. The working state length at rest and during a cough may range from about 25 to about 40 mm, for example about 30 mm. The working state width at rest and during a cough may range from about 25 to about 35 mm, for example about 30 mm. The removal state length may range from about 30 to about 50 mm, for example about 40 mm. The removal state width may range from about 15 to about 20 mm, for example about 18 mm.

For a straight stent, the working portion of the device has a length and equivalent diameter in the insertion state, the working state, and the removal state. The insertion state length may range from about 25 to about 60 mm, for example about 45 mm. The insertion state equivalent diameter may range from about 5 to about 20 mm, for example about 18 mm. The working state length at rest and during a cough may range from about 25 to about 60 mm, for example about 45 mm. The working state equivalent diameter at rest may range from about 20 to about 30 mm, for example about 25 mm. The working state equivalent diameter during a cough may range from about 15 to about 25 mm, for example about 20 mm. The removal state length may range from about 25 to about 60 mm, for example about 45 mm. The removal state equivalent diameter may range from about 15 to about 20 mm, for example about 18 mm.

For a rabbit stent, the working portion of the device has a length and equivalent diameter in the insertion state, the working state, and the removal state. The insertion state length may range from about 20 to about 30 mm, for example about 25 mm. The insertion state equivalent diameter may range from about 10 to about 20 mm, for example about 15 mm. The working state length at rest and during a cough may range from about 20 to about 30 mm, for example about 25 mm. The working state equivalent diameter at rest and during a cough may range from about 10 to about 30 mm, for example about 18 mm. The removal state length may range from about 20 to about 30 mm, for example about 25 mm. The removal state equivalent diameter may range from about 10 to about 20 mm, for example about 15 mm. The height of the working portion in all states may range from about 20 to about 30 mm, for example about 25 mm.

The anchoring portion of the device has a length and width in the insertion state, the working state, and the removal state. The insertion state length may range from about 20 to about 50 mm, for example about 30 mm. The insertion width may range from about 10 to about 20 mm, for example about 18 mm. The working state length at rest and during a cough may range from about 20 to about 50 mm, for example about 30 mm. The working state width at rest and during a cough may range from about 20 to about 60 mm, for example about 50 mm at the top and from about 10 to about 50 mm, for example about 25 mm at the bottom. The removal state length may range from about 20 to about 50 mm, for example about 30 mm. The removal state width may range from about 10 to about 20 mm, for example about 18 mm.

For a flower stent, the working portion of the device has a length and equivalent diameter in the insertion state, the working state, and the removal state. The insertion state length may range from about 20 to about 30 mm, for example about 25 mm. The insertion state equivalent diameter may range from about 10 to about 20 mm, for example about 15 mm. The working state length at rest and during a cough may range from about 20 to about 30 mm, for example about 25 mm. The working state equivalent diameter at rest may range from about 20 to about 35 mm, for example about 25 mm. The working state equivalent diameter during a cough may range from about 15 to about 30 mm, for example about 20 mm. The removal state length may range from about 20 to about 30 mm, for example about 25 mm. The removal state equivalent diameter may range from about 10 to about 20 mm, for example about 15 mm.

The anchoring portion of the device has a length and width in the insertion state, the working state, and the removal state. The insertion state length may range from about 20 to about 50 mm, for example about 30 mm. The insertion width may range from about 10 to about 20 mm, for example about 18 mm. The working state length at rest and during a cough may range from about 20 to about 60 mm, for example about 30 mm. The working state width at rest and during a cough may range from about 20 to about 60 mm, for example about 30 mm at the top and from about 10 to about 50 mm, for example about 20 mm at the bottom. The removal state length may range from about 20 to about 60 mm, for example about 30 mm. The removal state width may range from about 10 to about 20 mm, for example about 18 mm.

In one embodiment of the present invention, the working portion of the intravaginal devices is a stent. In other embodiments, the working portion may be a suppository, a vaginal tampon, a bladder support, and a combination thereof.

Elements of the devices of the present invention may be made from any elastic or supereleastic material. Suitable materials include, but are not limited to metals including metal alloys, for example a nickel-titanium ("NiTi") alloy known in the art as Nitinol. As is known in the art, there are a variety of ways to process NiTi, including resistance heating and permanent deformation to create a shape set. Other materials (other alloys, superelastic alloys or other NiTi compositions) may be utilized to make devices according to the present invention. Additionally, polymers including shape memory polymers (SMPs) may also be used in addition to or in place of the metals.

Shape memory is the ability of a material to remember its original shape, either after mechanical deformation, which is a one-way effect, or by cooling and heating which is a two-way effect. This phenomenon is based on a structural phase transformation. The first materials to have these properties were shape memory metal alloys including NiTi (Nitinol), CuZnAl (the first copper based SMA to be commercially exploited and the alloys typically contain 15-30 wt % Zn and 3-7 wt % Al), CuAlNi (may now be preferred to the CuZnAl; $Cu_{13}Al_4Ni$ is one that is often used commercially), CuAlBe (a $Cu_{12}Al$ doped with less than 0.5% of beryllium), and FeNiAl alloys. Strains of up to about 10% can be fully recovered in these alloys. Examples of suitable alloys further include Algiloy, Stainless Steel, for example 304 stainless steel, and carbon spring steels. The structure phase transformation of these materials is known as martensitic transformation.

SMPs are light, high in shape memory recovery ability, easy to manipulate and process, and economical compared to shape memory alloys. These materials are also useful for devices according to the present invention. There are few ways to achieve the shape memory properties. SMPs are characterized as phase segregated linear block co-polymers (e.g., thermoplastic elastomers) having a hard segment and soft segment that form physical cross-links. The hard segment is typically crystalline with a defined melting point, and the soft segment is typically amorphous with a defined glass transition temperature. The transition temperature of the soft segment is substantially less than the transition temperature of the hard segment. Examples of these materials include polyurethanes; polyether amides; polyether ester; polyester urethanes; polyether urethanes; and polyurethane/urea. SMPs are also formed by covalently cross-linked irreversible formation of the permanent shape. Different parameters that can be tailored for these materials are mechanical properties of permanent and temporary shape, customized thermal transitions, and kinetics of shape memory effect. SMPs can be biostable and bioabsorbable. Biostable SMPs are generally polyurethanes, polyethers, polyacrylates, polyamides, polysiloxanes, and their copolymers. Bioabsorbable SMPs are relatively new and include thermoplastic and thermoset materials. Shape memory thermosets may include poly (caprolactone) dimethacrylates; and shape memory thermoplastics may include combinations of different monomers to prepare polyester based copolymers.

When the SMP is heated above the melting point of the hard segment, the material can be shaped. This "original" shape can be memorized by cooling the SMP below the melting point of the hard segment. When the shaped SMP is cooled below the glass transition temperature of the soft segment while the shape is deformed, a new "temporary" shape is fixed. The original shape is recovered by heating the material above the glass transition temperature of the soft segment but below the melting point of the hard segment. The recovery of the original shape induced by an increase of temperature is called the thermal shape memory effect. Several physical properties of SMPs other than ability to memorize shape are significantly altered in response to external changes in temperature and stress, particularly at the glass transition of the soft segment. These properties include elastic modulus, hardness, and flexibility. The modulus of SMP can change by a factor of up to 200 when heated above the glass transition temperature of the soft segment. In order to prepare devices that will have sufficient stiffness, it is necessary to have thermal transitions such that the material will have high modulus at use temperature. For example, if a device is going to be used at body temperature, then the transition temperature may be higher than 37° C. (example 45-50° C.) so that upon cooling to 37° C. the modulus is high and thereby providing sufficient stiffness. It is also important to design the device such that it will compensate for lower physical properties compared to shape memory metal alloys. Some of the design features may include higher wall thickness; short connectors; or hinge points at appropriate locations. These materials can overcome some of the limitations with viscoelastic polymer properties such as creep and stress relaxation.

SMP can also be prepared by using TPEs prepared from hydrophilic polymers so that the phase transition can be also occur by physical changes due to moisture absorption. Examples of these TPEs are hydrophilic polymer ester amide (Pebax) and hydrophilic polyurethanes prepared by Elf Atochem and CardioTec International, respectively. Devices prepared from these materials will be soft and will be easier to remove after its use.

The shape memory materials may be formed of or at least enclosed within biocompatible materials, preferably materials that are approved for use in the human body. For example, medical grade silicone rubber may enclose a wire form device. This may be achieved through one or more tubular sheaths about the wire or as a coating prepared on the wire.

As indicated above, the device may be made as a uni-body construction, or it may be a composite device, e.g., the working portion and anchoring portion may be made separately and joined by attachment means, such as silicone tubing.

Additional elements features may be included to provide desired characteristics. In addition to improved biocompatibility, polymeric materials may cushion the device to minimize the risk of tissue damage.

For example, each working surface may have a pad 30 to distribute the forces directed toward the vaginal walls, thereby reducing the unit pressure applied by the device. This soft, resilient cushion could be made out of various types of medical grade sponges and foams (such as those formed from HYPOL™ Hydrophilic Polyurethane Prepolymers from Dow Chemical Company), thermoplastic elastomers, silicones, fibers, and the like.

Figure 8:
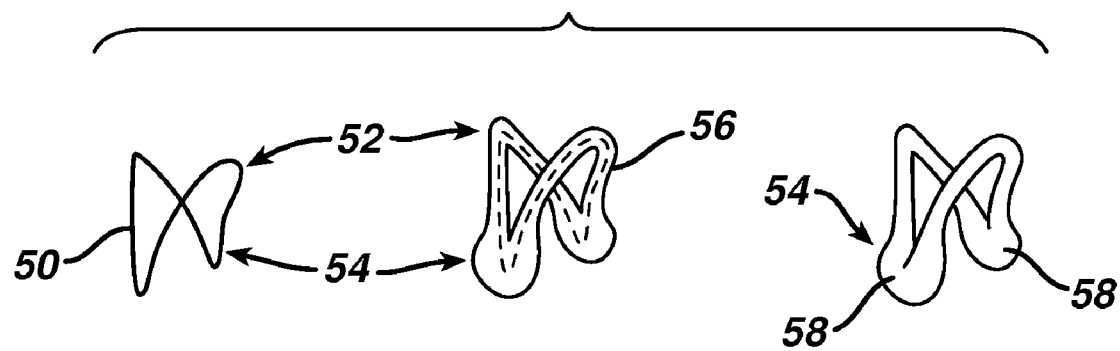
FIG. 8 shows a bare wire form formed into an elastic structure and a coated wire form.

As shown in FIG. 8, the device includes a wire form 50 formed into an elastic structure having an anchoring portion 52 and a working portion 54. The wire form 50 has a biocompatible polymer coating 56 disposed thereon. In the device of FIG. 8, the coating 56 has enlarged regions, each forming a pad 58 on one of the working surfaces of the working portion 54.

Figure 9A:
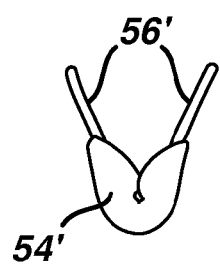
FIG. 9A-9C shows three alternative embodiments of a composite intravaginal device.
Figure 9B:
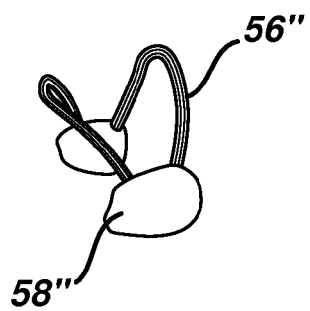
Figure 9C:
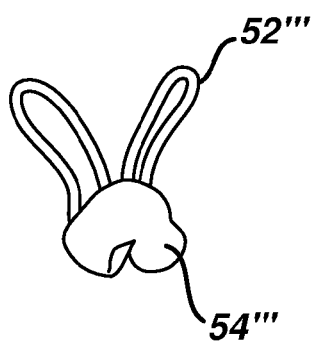

In the alternative embodiments shown in FIG. 9A, the device may replace the full coating of FIG. 8 with tubing 56' and a single compressible foam working portion 54'. The embodiment of FIG. 9B, employs two separate pad elements 58" as the working portion 54". The wire form 50" that extends to form the anchoring portion 52" provides elasticity to the pad elements 58" to support the urinary system. The embodiment of FIG. 9C incorporates the Rabbit stent anchoring portion 52''' and replaces the working portion wire form with an enlarged pad structure 54'''. Again, this enlarged pad structure may be formed of any appropriate resilient material including foams, fibrous structures, and the like.

In addition, the pessary 10 may be loaded with various pharmacological compounds and additives, such as hormones and/or alpha-adrenoceptor agonists, urethra selective stimulators, prostaglandins, anticholinergics, hormones, nicotine, cytostatics, tranquilizers, local anaesthetics and other compounds, such as pharmacologically active alpha-[tertiary-aminomethyl]-benzenemethanol derivatives and other compounds as disclosed in U.S. Pat. No. 5,527,821 to Willman et al., as well as toxin inhibitors such as glyceryl monolaurate and related compounds as disclosed in Brown-Skrobot et al., U.S. Pat. No. 5,547,985, each of which is incorporated by reference herein.

Methods of associating drugs, hormones or other pharmacological compounds with an object for drug administration to the body are well known to those skilled in the art, as for example, described in U.S. Pat. No. 5,188,835 and German Patent No. 198 29 713, both incorporated in their entirety by reference herein. In still a further embodiment, topical medications, ointments or creams can be associated with pessary 10 by infusion (injection), coating or absorption into the pores of a sponge-like material of the medication of the pessary 10 and slowly released, within a day or two, into the vaginal cavity. This embodiment of the invention may be used for treating dryness, irritation, or other local conditions. The ointment, cream, etc., can be replenished into the pessary on an as needed basis.

Figure 10:
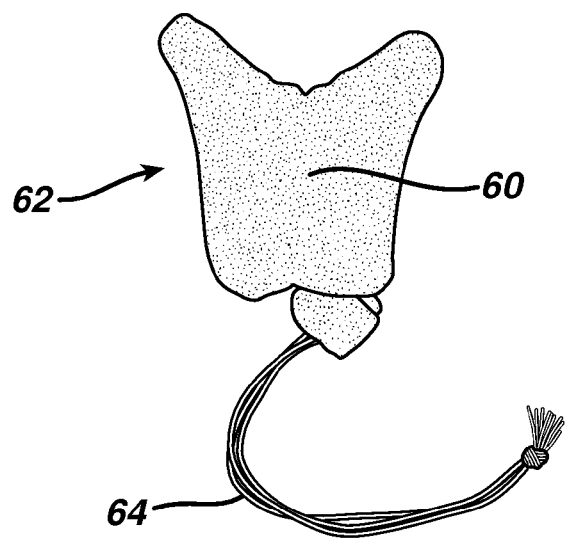
FIG. 10 is a device in a bag that is useful for the present invention.

As shown in FIG. 10, the intravaginal devices also may be enclosed in a sheet-like material 60 that may reduce friction during deployment, shield a wire form from view (to be aesthetically pleasing), help control the device during insertion and removal, help the device to stay in place, and/or create more contact area for applying pressure to the bladder neck. The sheet-like material may be formed into a cover or flexible bag 62 that may also provide increased friction against the vaginal epithelium in comparison to a silicone-coated wire form to reduce the likelihood of undesired movement during use, e.g., becoming skewed. Any medically appropriate sheet-like materials may be used to form the cover or bag, and depending upon the desired end-use, it may be opaque, light, and/or breathable. Useful sheet-like materials include those used in the manufacture of tampons, such as nonwoven fabrics and plastic film, including apertured films. The cover or bag itself may also be apertured.

The device may be removed using a removal string 64 that is criss-crossed between the struts of the device to create a "cinch sac" mechanism. Any string known in the sanitary protection art may be useful for this purpose. As the strings are pulled during removal, the struts are gathered together to create a smaller diameter device during removal. Cinching the device at its base makes removal of the device more comfortable and easier as it makes the diameter of the device smaller and the shape conducive to remove easily.

The device may be inserted using an applicator 66 similar to those known in the tampon art as shown in FIG. 2. The applicator may be a push-type applicator or a retractable applicator. A collar 68 may be added to control the depth of insertion. The applicator may be dipped in a lubricant and is placed into the vagina until the base of the applicator is at the opening of the vagina. The applicator may be oriented with an orientation indicator pointing up. This is because some devices that are useful in the method of the present invention require orientation to provide maximum efficacy.

After the user orients the applicator, the plunger then is pushed to its maximum extent, or until the subject feels comfortable. The plunger and barrel are then removed from the body. If the device is not placed properly, the device may be pulled or pushed to the correct location. The device may be left in place for as long as medically recommended. For example, the device may be used for a period of about 4 to about 24 hours and then removed and discarded.

The method of insertion is designed to provide comfortable and easy insertion, accurate placement, proper orientation, good ergonomics, and to be aesthetically-pleasing.

Women can be screened for having stress urinary incontinence to determine if the method of the present invention is suitable using a simple 3-day voiding diary. The 3-day voiding diary records amount urinated in toilet, urine loss beyond control, amount of urine loss, description of urine loss to be stress, urge, or both, if the loss was bothersome, and fluid intake amount. Using this data, one can assess whether she has primarily stress, urge, or mixed urinary incontinence.

EXAMPLES

The following examples are illustrative of devices according to the present invention. The claims should not be construed to be limited to the details thereof.

Prototype devices were modeled in shape and scale after existing, predicate vaginal pessary devices. There were two geometries presented for this device. The expanded stent device was approximately 35 mm in diameter and 55 mm long. The first of the proposed geometries was a simple S-shaped stent like a ring; the second resembled the form of a handled basket and was modeled in the form of the classic "ring" pessary. In its design the "basket" portion was approximately 25 mm high and the "handle" made up the balance of the overall length.

Both are assemblies of four known medical materials. The collapsed vaginal stents were enclosed in a commercial plastic tampon applicator. The working assemblies were made up of a nickel-titanium wire form (Nitinol), which was covered by a medical grade silicone rubber (silastic) tube. This covered wire form "stent" was placed in a heat-sealed bag made of the same standard non-woven polypropylene material used in tampon covers. This covered device was made to be easily removable by the addition of a tampon cotton string, as a cinch and removal pull.

The nickel-titanium wire used in these prototypes was the same alloy as used in vascular systems. Post-shape-setting processing of the metal does not effect corrosion and biocompatibility of the device. The silicone tubing was also a known medical grade material. The silastic tubing was Dow Q7-4750.

The general procedure was to shape an SE508 NiTi into the design on a form using one or multiple steps heating the fixture and form to about 500° C. for at least one minute for each step. Any excess wire was cut from the form. As is known in the art, the wire may be chemically etched to provide further biocompatibility. The wire was enclosed in a rubbery polymer coating such as silicone assuring to fasten the wire ends such that they may not puncture the surface.

Example 1

Rabbit Flat Pessary

Figure 11:
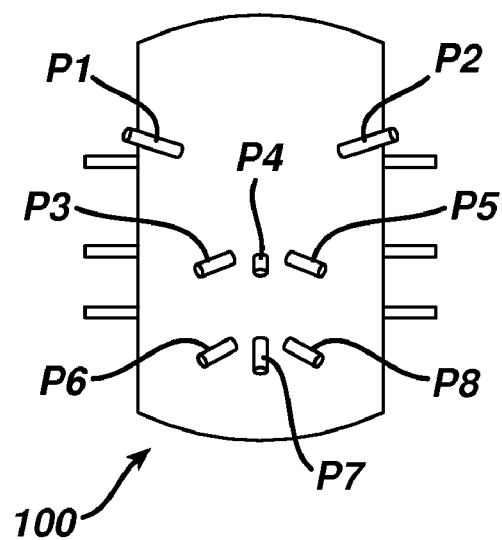
FIG. 11 illustrates a tool utilized to form the devices utilized in the present invention.
Figure 12:
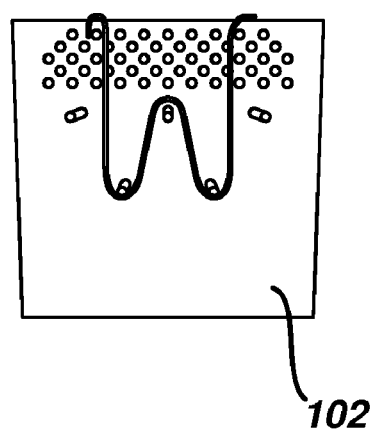
FIG. 12 illustrates a tool utilized to heat-treat the devices utilized in the present invention.
Figure 13:
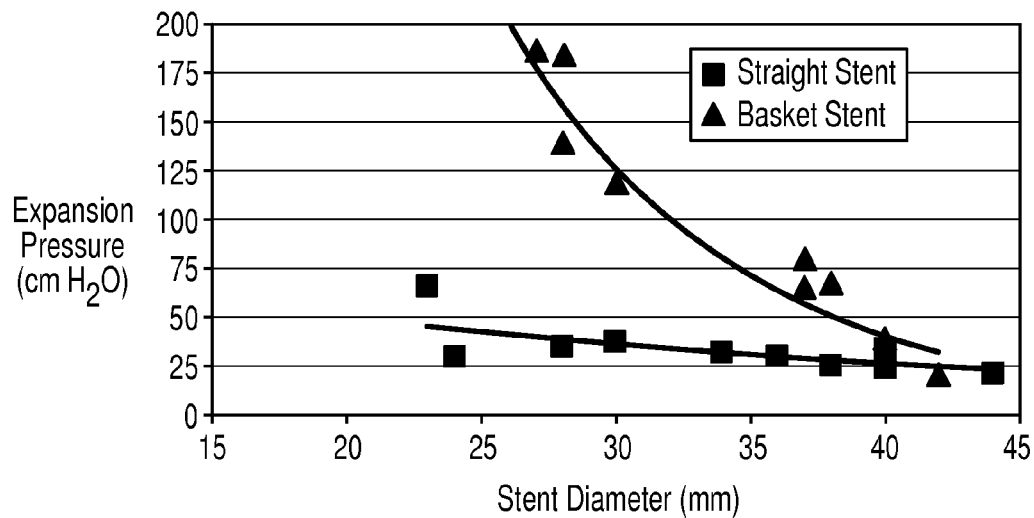
FIG. 13 shows a diameter vs. pressure curve for a straight stent and a basket stent as described herein.
Figure 14:
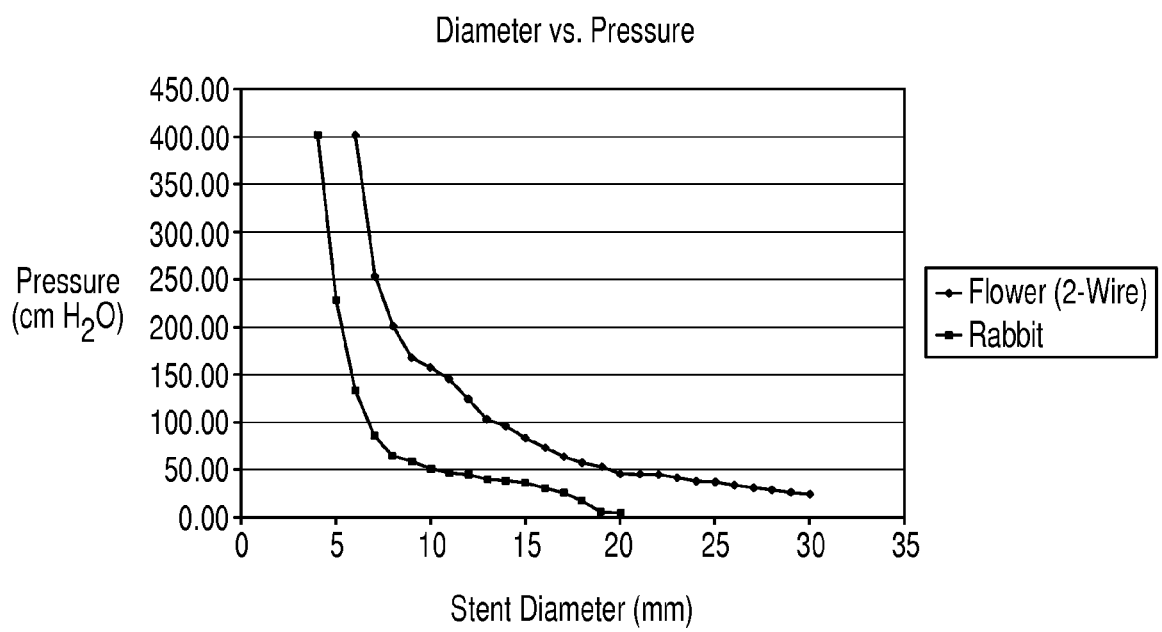
FIG. 14 shows a graph of the diameter versus pressure of a rabbit and flower stent.
Figure 15:
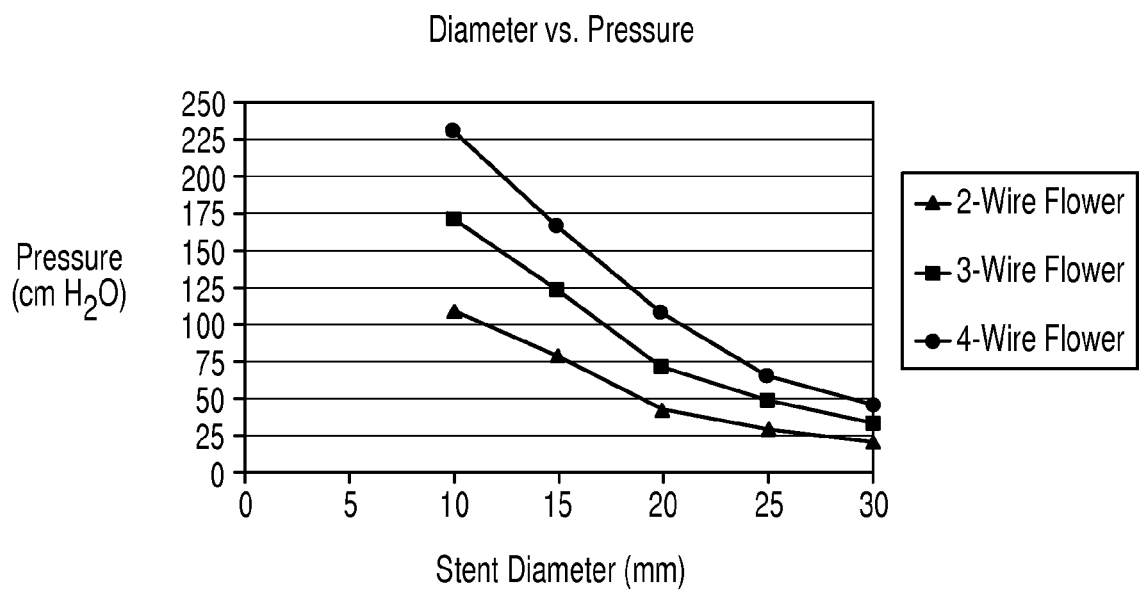
FIG. 15 shows a graph of the diameter versus pressure of three different pressure levels of the flower stent.
Figure 16:
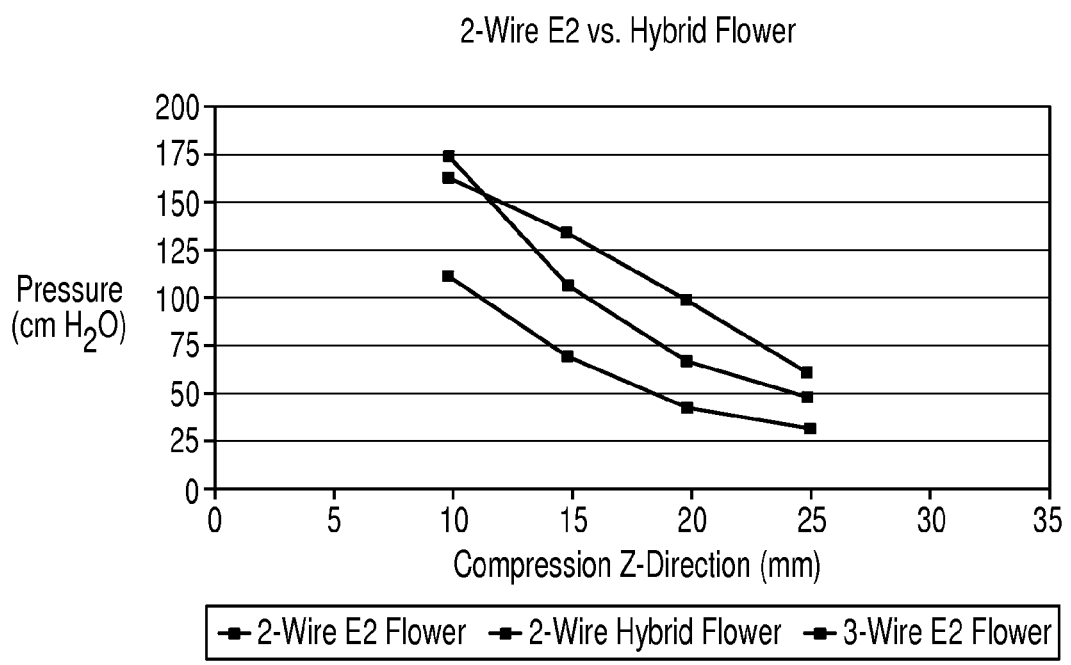
FIG. 16 shows a graph comparing the diameter versus pressure curve of two different pressure levels of the flower stent against a hybrid foam-wire device.

Approximately 1 foot of straightened and etched SE508 wire, 0.0315" diameter was obtained. The tool 100 pictured in FIG. 11 was made using conventional techniques known in stent art. In a smooth upswing, the wire was wrapped around the pins in the following order to create the pattern: P7, P3, PLCC, P3, P6 CC, P3, P6, P4, P8 CC, P5, P8, P5, P2 CC, P5, P7, PLCC, P3, P7 (the wrapping was clockwise, unless indicated by "CC"). The zigzag wrapping pattern was smoothly discontinued and the final end of the wire was poked through holes in the fixture to secure it. A large hose clamp was wrapped around the fixture, over the zigzag portion. The clamp was tightened to keep the wires in position, but not so much as to compress the wires to the surface of the fixture. The wound wire was heat treated on the fixture for 3 minutes in a 505 C (calibrated) salt pot, then quenched with water. The heat-treated wire was removed from the fixture by unwinding it. The wire was trimmed at point P3 allowing for overlap along the "ear" and the overlapping wires were wrapped to hold them together with NiCr wire. A secondary heat treatment fixture 102 shown in FIG. 12 was made according to methods known in the art. The wire was aligned to form onto the fixture. The ends of the wire were ground to remove sharp and jagged edges.

The wire form component was passivated by methods known in the art to optimize biocompatibility. Some wire form components were etched or chemically processed to optimize biocompatibility. The parts were moved to a clean room and dipped in denatured alcohol before being placed on a clean table. All tools were cleaned with isopropyl alcohol as well as gloved hands before touching parts from denatured alcohol solution. Tubing was cleaned with Isopropyl alcohol by dripping through with a disposable pipette. The tube was dried by wicking onto a paper towel. The tube was filled with 2-4 inches of lubricant mineral oil from a syringe. Pressed fingers were run along the tube to spread the oil evenly along the inside. The tubing was slid over the wire carefully paying attention that the wire ends did not poke through the tubing. The tubing was pulled back to expose both wire ends. The ends were lined up so that the ear rests naturally. Forceps were used to hold the tubing back from the wire ends. Shrink tube was placed across the wire ends and heated to hold wire ends in place. The tubing was slid over the shrink tube section. Tubing ends were overlapped by at least 0.5 cm by pressing the ends together.

Example 2

Flower Flat Pessary

Approximately 1 foot of straightened and etched SE508 wire, 0.0315" diameter was obtained. The tool 100 pictured in FIG. 11 was made using conventional techniques known in stent art. In a smooth upswing, the wire was wrapped around the pins in the following order to create the pattern: P6, P3, PLCC, P3, P6, P4, P7, P6, P3, PLCC, P3, P6, P4, P7, P5, P2 CC, P5, P7, P4, P6, P3, P1CC, P3, P5, P2 CC, P5, P7, P4, P6, P3, P1CC, and P3. For a two-wire device, the pattern was repeated. The starting point may be adjusted to move the wire ends to a different location. The zigzag-wrapping pattern was smoothly discontinued and the final end of the wire was poked through holes in the fixture to secure it. A large hose clamp was wrapped around the fixture, over the zigzag portion. The clamp was tightened to keep the wires in position, but not so much as to compress the wires to the surface of the fixture. The wound wire was heat treated on the fixture for 3 minutes in a 505 C (calibrated) salt pot, then quenched with water. The heat-treated wire was removed from the fixture by unwinding it. The wire was trimmed at point P3 allowing for overlap along the "ear" and the overlapping wires were wrapped to hold them together with NiCr wire. A secondary heat treatment fixture 102 shown in FIG. 12 was made according to methods known in the art. The wire was aligned to form onto the fixture. The ends of the wire were ground to remove sharp and jagged edges. The wire form component was passivated by methods known in the art to optimize biocompatibility. Some wire form components were etched or chemically processed to optimize biocompatibility. The parts were moved to a clean room and dipped in denatured alcohol before being placed on a clean table. All tools were cleaned with isopropyl alcohol as well as gloved hands before touching parts from denatured alcohol solution. Tubing was cleaned with Isopropyl alcohol by dripping through with a disposable pipette. The tube was dried by wicking onto a paper towel. The tube was filled with 2-4 inches of lubricant mineral oil from a syringe. Pressed fingers were run along the tube to spread the oil evenly along the inside. The tubing was slid over the wire carefully paying attention that the wire ends did not poke through the tubing. The tubing was pulled back to expose both wire ends. The ends were lined up so that the ear rests naturally. Forceps were used to hold the tubing back from the wire ends. Shrink tube was placed across the wire ends and heated to hold wire ends in place. The tubing was slid over the shrink tube section. Tubing ends were overlapped by at least 0.5 cm by pressing the ends together.

Example 3

Multi-Wire Flower Pessary

The level of severity of incontinence varies greatly from woman to woman and changes throughout a woman's life. Mechanically, this level is determined by the support of the pelvic floor musculature. When this muscle system is weakened, the urethra does not properly close when intra-abdominal pressure is exerted onto the bladder. In order to address the various levels of support of the pelvic floor musculature, there are three pressure levels of the device: Pressure 1 (for women who need minimal amount of support), Pressure 2 (for moderate support), and Pressure 3 (for women who need the greatest support).

To test this concept, the device of Example 2 was reproduced in these three different pressure levels: Pressure 1 was formed with two wires generally as described above in Example 2; Pressure 2 was formed with three wires; and Pressure 4 was formed with four wires.

Example 4

Composite Flower Pessary

The device of Example 2 was reproduced with the wire form working portion with a pair of separate foam pad elements. The wire form that extends to form the anchoring portion provides elasticity to the pad elements to support the urinary system.

Each of the exemplary devices were tested to determine the outward pressure exerted as it expands from a compressed state as described below, and the resulting diameter vs. pressure curves are shown in FIGS. 13-16.

Expansion Pressure Test

The expansion pressure test was used to determine the outward pressure the device was able to exert as it expanded from its compressed insertion state to its deployed or use state in the body. Equilibrium of the expansion pressure and the internal resistance of the body determined the diameter of the device in place.

The outward pressure the device exerts at various compression states (insertion, during use at rest, and during use under stress) was measured using a simple linear scale (Mettler PK 4800 scale). The pressure the device exerted as well as the diameter of the device were measured and recorded.

The device is tested by placing the device between the scale and a custom-made arm that compresses the device at known, incremental distances, measured in mm. The device was measured first at its free state (i.e., for rabbit: 20 mm) and then slowly compressed in increments (i.e. 1 mm or 5 mm). The force that the device exerts on the scale at known compression increments was measured in grams. The pressure was calculated by converting the force measurement from grams to pounds-force. The pounds-force was then converted to PSI units by dividing the pound-force by the contact area of the device. The contact area of the device was defined as the working portion of the device. The PSI units were then converted into cm $H_2O$ pressure. The resulting device diameter (mm) versus pressure (cm $H_2O$) was then graphed.

This Pressure Curve Slope illustrates outward pressure that the device exerts on the body varies with device compression. This pressure increases as compression increases and reduces as the device is unloaded. This is an important behavior of our device because at rest, the pressure in the vagina is low (approximately 35 cm $H_2O$). When a woman has a stress event such as coughing or sneezing, high intra-abdominal pressure as much as over 140 cm $H_2O$ is exerted on the bladder in a very short time period. When this event occurs, the device needs to quickly react to this sudden increase in pressure.

When the device is at rest, the device is compressed to about 20-25 mm. When a sudden intra-abdominal pressure is exerted on the device, the device is compressed down to 10-15 mm. At rest, it is important to that the pressure that the device exerts on the body is low for comfort and safety. When the device is compressed during high intra-abdominal pressure events, the device needs to exert adequate pressure quickly and then relax to its original low resting pressure when the stress event is completed.

The devices similar to those of Example 3 may be used to illustrate the desired dynamic elasticity of the intravaginal urinary incontinence device. The following table illustrates desired Expansion Pressure targets when the Low-, Medium-, and High-support devices are compressed to the specified diameter—e.g., a Resting Diameter of 25 mm or a Compressed Diameter of 10 mm.

| Device | # of Wires | Pressure at 25 mm Resting Diameter (cm $H_2O$) | Pressure at 10 mm Compressed Diameter (cm $H_2O$) |
|---|---|---|---|
| Low | 2 | 25 | 100 |
| Moderate | 3 | 50 | 175 |
| High | 4 | 75 | 225 |

More generally, the elastic working portion preferably has a first use equivalent diameter (a "Resting Diameter") of at least about 15 mm under an expansion pressure of 20 cm $H_2O$. This reflects the device under normal use conditions. A more preferred first use equivalent diameter is at least about 20 mm under an expansion pressure of 35 cm $H_2O$.

A second use equivalent diameter of about 5 to about 25 mm under an expansion pressure of 100 cm $H_2O$ reflects the device under stress use conditions, such as a sneeze. A more preferred second use equivalent diameter is at least about 10 mm under an expansion pressure of 140 cm $H_2O$.

Preferably, the second use equivalent diameter is less than the first use equivalent diameter. More preferably, the second use equivalent diameter is less than the first use equivalent diameter and at least about 20% of the first use equivalent diameter.

A third use equivalent diameter of about 10 to about 20 under expansion pressure of 150 cm $H_2O$ reflects severe stress use conditions.

Use Test

A use test was performed with 8 women to determine the efficacy of commercially available urinary incontinence products. A commercially available ring pessary, a commercially available contiform pessary, and a commercially available tampon were inserted and tested. The first test was a stress test. For this test, the woman coughed 3 hard times while holding a commercially available c-fold paper towel against her perineum. Urine leak was weighed and compared without the device to with the device. A physician assessed the ability of the device to stay in place by holding the subject's labia apart while the subject coughed, and observing if the device moved. If the device moved passed the bladder neck (towards the introitus), it was considered to not stay in place. Subjects were also asked to rate comfort upon insertion and removal. The results of this study are shown in Table 1 below.

TABLE 1

| Device | Stayed in Place | Percent of Women With Reduction | Comfortable Insertion | Comfortable Removal |
|---|---|---|---|---|
| Ring Pessary | 6 out of 7 | 71 | 4 out of 6 | 5 out of 6 |
| Contiform | 5 out of 6 | 83 | 4 out of 8 | 6 out of 8 |
| Tampon | 7 out of 8 | 25 | 8 out of 8 | 8 out of 8 |

Based on the data above, it was determined that there is an opportunity to provide urinary incontinence devices with improved stay in place and efficacy.

A second use test was performed with a different set of 10 women. A straight stent having an overall height of 55 mm and a initial diameter of 95 mm made from Nitinol wire (3 strands of 0.0315 inches) and a basket stent of FIG. 6. The straight stent was placed in a nonwoven bag and compressed to 45 mm. The basket stent was 65 mm in overall height and had an initial diameter of 45 mm made from Nitinol wire (2 strands of 0.0315 inches). It was compressed to 35 mm in a nonwoven bag. Both were tested as described above. The results are shown in Table 2 below.

TABLE 2

| Device | Stayed in Place | Percent of Women With Reduction | Comfortable Insertion | Comfortable Removal |
| --- | --- | --- | --- | --- |
| Straight | 4 out of 10 | 20 | 7 out of 10 | 8 out of 10 |
| Basket | 6 out of 9 | 56 | 6 out of 10 | 6 out of 10 |

A third use test was performed with a different set of 12 women. A flower stent (Example 2 FIG. 4) having an overall height of 45 mm and a initial diameter of 45 mm made from Nitinol wire (2 strands of 0.0315 inches) and a rabbit stent (Example 1, FIG. 1). The flower stent was placed in a nonwoven bag and compressed to 35 mm. The rabbit stent was 50 mm in overall height and had an initial diameter of 20 mm made from Nitinol wire (1 strand of 0.0315 inches). It was placed in a nonwoven bag. Both were tested as described above. The results are shown in Table 3 below.

TABLE 3

| Device | Stayed in Place | Percent of Women With Reduction | Comfortable Insertion | Comfortable Removal |
| --- | --- | --- | --- | --- |
| Flower | 12 out of 12 | 67 | 12 out of 12 | 12 out of 12 |
| Rabbit | 12 out of 12 | 58 | 12 out of 12 | 12 out of 12 |

The results above show an improvement in stay in place as well as comfortable insertion and removal. It was also determined that the devices tested in Table 3 reduced the amount of urine leaked significantly. The percent urine leakage reduction was 79 for the rabbit stent and 73 for the flower stent. The percent urine leakage reduction for the basket stent was 69.

We claim:

1. A method for treating a urinary incontinent female comprising the steps of:
   a) inserting into the female's vagina a first disposable device comprising a working portion having opposed working surfaces, a first surface disposed toward an associated urinary system and a second surface disposed opposite thereof and a distance between these opposed working surfaces defining a working portion equivalent diameter, to provide support to an associated urinary system having a first use equivalent diameter, measured between the first and second surfaces, of at least about 15 mm under an expansion pressure of 20 cm $H_2O$ and a second use equivalent diameter, measured between the first and second surfaces, of about 5 to about 25 mm under an expansion pressure of 100 cm $H_2O$ wherein the second use equivalent diameter is less than the first use equivalent diameter;
   b) removing the first disposable device;
   c) inserting into the female's vagina a second disposable device substantially identical to the first disposable device.

2. The method according to claim 1, wherein the first disposable device further comprises an anchoring portion to maintain the device in place during use.

3. The method according to claim 2, wherein the anchoring portion is arranged and configured to engage walls of the female's vagina.

4. The method according to claim 2, wherein the anchoring portion comprises at least two extensions beyond the at least one end of the working portion.

5. The method according to claim 2, wherein the anchoring portion comprises a shape selected from the group consisting of a basket handle, a dog bone, a rabbit ear, and combinations thereof.

6. The method according to claim 5, wherein the anchoring portion comprises a rabbit ear shape and the method further comprises the step of arranging one rabbit ear portion in a lateral vaginal fornix and another rabbit ear portion in an opposite lateral vaginal fornix with the female's cervix disposed between the rabbit ear portions, wherein the rabbit ear portions engage vaginal fornix walls.

7. The method according to claim 1, wherein the working portion comprises an elastic structure selected from the group consisting of a slotted tube, a wire form, and combinations thereof.

8. The method according to claim 7, wherein the wire form comprises a plurality of struts that at least partially define and support opposed working surfaces.

9. The method according to claim 8, wherein the working portion further comprises a withdrawal string, a proximal end of which is operatively connected to at least two struts and is arranged and configured such that tension on a distal end of the withdrawal string urges the opposed working surfaces together.

10. The method according to claim 9, further comprising the steps of pulling on the withdrawal string to urge the opposed faces together; and withdrawing the first disposable device from the female's vagina.

11. The method according to claim 1, wherein the working portion further comprises a pad associated with each of the working surfaces.

12. The method according to claim 1, wherein the elastic working portion comprises a material selected from the group consisting of polymers, metals, and combinations thereof.

13. The method according to claim 11, wherein the pad comprises a material selected from the group consisting of sponges and foams, thermoplastic elastomers, silicones, fibers, and combinations thereof.

14. The method according to claim 1, wherein the working portion has a first end disposed toward a cervix associated with the vagina and a second end, opposite the first end, disposed toward an external opening of the vagina and wherein the anchoring portion extends beyond at least one of the first and second ends of the working portion.

* * * * *